US009453067B2

(12) United States Patent
Deutel et al.

(10) Patent No.: US 9,453,067 B2
(45) Date of Patent: Sep. 27, 2016

(54) STABLE PHARMACEUTICAL LIQUID FORMULATIONS OF THE FUSION PROTEIN TNFR:FC

(75) Inventors: Britta Deutel, Kundl (AT); Thomas Lauber, Kundl (AT); Sabine Fuertinger, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/112,587

(22) PCT Filed: Apr. 19, 2012

(86) PCT No.: PCT/EP2012/057119
§ 371 (c)(1),
(2), (4) Date: Mar. 6, 2014

(87) PCT Pub. No.: WO2012/143418
PCT Pub. Date: Oct. 26, 2012

(65) Prior Publication Data
US 2014/0186351 A1    Jul. 3, 2014

(30) Foreign Application Priority Data
Apr. 20, 2011   (EP) .................................... 11163171

(51) Int. Cl.
| A61K 38/16 | (2006.01) |
| C07K 14/705 | (2006.01) |
| C07K 14/715 | (2006.01) |
| A61K 47/12 | (2006.01) |
| A61K 47/18 | (2006.01) |
| A61K 38/17 | (2006.01) |

(52) U.S. Cl.
CPC ....... *C07K 14/7151* (2013.01); *A61K 38/1793* (2013.01); *A61K 47/12* (2013.01); *A61K 47/183* (2013.01); *C07K 2319/30* (2013.01)

(58) Field of Classification Search
None
See application file for complete search history.

(56) References Cited

U.S. PATENT DOCUMENTS

| 2005/0032183 A1* | 2/2005 | Osslund et al. ............... 435/183 |
| 2006/0292148 A1 | 12/2006 | Matsumoto |
| 2008/0071063 A1* | 3/2008 | Allan et al. ................. 530/387.1 |
| 2008/0187544 A1* | 8/2008 | Burkly et al. ............. 424/158.1 |

FOREIGN PATENT DOCUMENTS

| EP | 0 420 649 A2 | 4/1991 |
| EP | 1 314 437 A1 | 5/2003 |
| EP | 1 478 394 B1 | 7/2008 |
| JP | 2005-527503 | 9/2005 |
| JP | 2009-525986 | 7/2009 |
| WO | WO 00/62790 A2 | 10/2000 |
| WO | WO 03/072060 A2 | 9/2003 |
| WO | WO 2005/012353 A1 | 2/2005 |
| WO | WO 2005/082377 A1 | 9/2005 |
| WO | WO 2007/092772 A2 | 8/2007 |
| WO | WO 2011/141926 A2 | 11/2011 |

OTHER PUBLICATIONS

Baynes et al., Role of Arginine in the Stabilization of Proteins against Aggregation. Biochem. Mar. 29, 2005;44(12):4919-25.
Bolli et al., L-Proline reduces IgG dimer content and enhances the stability of intravenous immunoglobulin (IVIG) solutions. Biologicals. Jan. 2008;38(1):150-7.
Kolhe et al., Impact of Freezing on pH of Buffered Solutions and Consequences for Monoclonal Antibody Aggregation. Biotechnol Prog. May-Jun. 2010;26(3):727-33.
Shiraki et al., Biophysical Effect of Amino Acids on the Prevention of Protein Aggregation. J Biochem. Oct. 2002;132(4):591-5.
Zheng et al., Influence of pH, buffer species, and storage temperature on physiochemical stability of a humanized monoclonal antibody LA298. Int J Pharm. Feb. 3, 2006;308(1-2):46-51.
PCT/EP2012/057119, Jul. 5, 2012, International Search Report and Written Opinion.
PCT/EP2012/057119, Oct. 22, 2013, International Preliminary Report on Patentability.
Third Party Observations for EP 12715107.4 filed Dec. 4, 2013.

* cited by examiner

*Primary Examiner* — Michael Pak
(74) *Attorney, Agent, or Firm* — Wolf, Greenfield & Sacks, P.C.

(57) ABSTRACT

The present invention relates to stable pharmaceutical liquid formulations of the fusion protein TNFR:Fc comprising different buffer systems and stabilizers. In particular, it could be demonstrated that the physical stability of TNFR:Fc is significantly improved by using a citrate buffer system and lysine as stabilizer.

16 Claims, No Drawings

SEQUENCE LISTING

<160> NUMBER OF SEQ ID NOS: 4

<210> SEQ ID NO 1
<211> LENGTH: 455
<212> TYPE: PRT
<213> ORGANISM: homo sapiens

<400> SEQUENCE: 1

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu

```
                245                 250                 255
Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 2
<211> LENGTH: 461
<212> TYPE: PRT
<213> ORGANISM: homo sapiens

<400> SEQUENCE: 2

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160
```

-continued

```
Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
        180                 185                 190

Asn Ala Ser Met Asp Ala Val Cys Thr Ser Thr Pro Thr Arg Ser
            195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
                260                 265                 270

Leu Leu Ile Ile Gly Val Val Asn Cys Val Ile Met Thr Gln Val Lys
                275                 280                 285

Lys Lys Pro Leu Cys Leu Gln Arg Glu Ala Lys Val Pro His Leu Pro
        290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Gly Ala Gly Glu Ala Arg Ala Ser Thr Gly Ser Ser
                355                 360                 365

Asp Ser Ser Pro Gly Gly His Gly Thr Gln Val Asn Val Thr Cys Ile
                370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Glu Lys Pro
                435                 440                 445

Leu Pro Leu Gly Val Pro Asp Ala Gly Met Lys Pro Ser
                450                 455                 460

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 467
<212> TYPE: PRT
<213> ORGANISM: artificial
<220> FEATURE:
<223> OTHER INFORMATION: Etanercept

<400> SEQUENCE: 4

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

```
Arg Leu Cys Ala Pro Leu Arg Lys Cys Arg Pro Gly Phe Gly Val Ala
        115             120             125
Arg Pro Gly Thr Glu Thr Ser Asp Val Val Cys Lys Pro Cys Ala Pro
        130             135             140
Gly Thr Phe Ser Asn Thr Thr Ser Ser Thr Asp Ile Cys Arg Pro His
145             150             155             160
Gln Ile Cys Asn Val Val Ala Ile Pro Gly Asn Ala Ser Met Asp Ala
                165             170             175
Val Cys Thr Ser Thr Ser Pro Thr Arg Ser Met Ala Pro Gly Ala Val
                180             185             190
His Leu Pro Gln Pro Val Ser Thr Arg Ser Gln His Thr Gln Pro Thr
        195             200             205
Pro Glu Pro Ser Thr Ala Pro Ser Thr Ser Phe Leu Leu Pro Met Gly
        210             215             220
Pro Ser Pro Pro Ala Glu Gly Ser Thr Gly Asp Glu Pro Lys Ser Cys
225             230             235             240
Asp Lys Thr His Thr Cys Pro Pro Cys Pro Ala Pro Glu Leu Leu Gly
                245             250             255
Gly Pro Ser Val Phe Leu Phe Pro Pro Lys Pro Lys Asp Thr Leu Met
                260             265             270
Ile Ser Arg Thr Pro Glu Val Thr Cys Val Val Val Asp Val Ser His
        275             280             285
Glu Asp Pro Glu Val Lys Phe Asn Trp Tyr Val Asp Gly Val Glu Val
        290             295             300
His Asn Ala Lys Thr Lys Pro Arg Glu Glu Gln Tyr Asn Ser Thr Tyr
305             310             315             320
Arg Val Val Ser Val Leu Thr Val Leu His Gln Asp Trp Leu Asn Gly
                325             330             335
Lys Glu Tyr Lys Cys Lys Val Ser Asn Lys Ala Leu Pro Ala Pro Ile
                340             345             350
Glu Lys Thr Ile Ser Lys Ala Lys Gly Gln Pro Arg Glu Pro Gln Val
        355             360             365
Tyr Thr Leu Pro Pro Ser Arg Glu Glu Met Thr Lys Asn Gln Val Ser
        370             375             380
Leu Thr Cys Leu Val Lys Gly Phe Tyr Pro Ser Asp Ile Ala Val Glu
385             390             395             400
Trp Glu Ser Asn Gly Gln Pro Glu Asn Asn Tyr Lys Thr Thr Pro Pro
                405             410             415
Val Leu Asp Ser Asp Gly Ser Phe Phe Leu Tyr Ser Lys Leu Thr Val
                420             425             430
Asp Lys Ser Arg Trp Gln Gln Gly Asn Val Phe Ser Cys Ser Val Met
        435             440             445
His Glu Ala Leu His Asn His Tyr Thr Gln Lys Ser Leu Ser Leu Ser
        450             455             460
Pro Gly Lys
465
```

STABLE PHARMACEUTICAL LIQUID FORMULATIONS OF THE FUSION PROTEIN TNFR:FC

RELATED APPLICATIONS

This application is a national stage filing under 35 U.S.C. 371 of International Application PCT/EP2012/057119 entitled "STABLE PHARMACEUTICAL LIQUID FORMULATIONS OF THE FUSION PROTEIN TNFR:Fc," filed Apr. 19, 2012, which claims priority to EP Application No. 1163171.9, filed Apr. 20, 2011, the entire disclosure of each of which is incorporated by reference herein in its entirety.

The present invention relates to stable pharmaceutical liquid formulations of the fusion protein TNFR:Fc comprising different buffer systems and stabilizers. In particular, it could be demonstrated that the physical stability of TNFR:Fc is significantly improved by using a citrate buffer system and lysine and/or proline as stabilizer.

BACKGROUND OF THE INVENTION

Commercial antibodies are commonly formulated in phosphate buffer. Also TNFR:Fc is commonly buffered in sodium phosphate (EP1478394, WO 03/072060 A2). Currently, e.g. the TNFR:Fc protein Etanercept is marketed under the tradename Enbrel® having a composition as shown in Table 1.

TABLE 1

Composition of Etanercept (Enbrel®)

|  | [mg/mL] | [mM] |
| --- | --- | --- |
| Etanercept | 50 | 0.3 |
| Sucrose | 10 | 29 |
| Sodium chloride | 5.8 | 100 |
| L-arginine hydrochloride | 5.3 | 25 |
| Sodium phosphate monobasic | 2.6 | 19 |
| Sodium phosphate dibasic | 0.9 | 6 |
| WFI | ad 0.5/1.0 ml | |
| pH | 6.3 ± 0.2 | |

Aggregation of antibody products can be controlled by the addition of small amphiphilic molecules. Thereof, L-arginine is the amino acid of choice in suppressing protein interactions in commercial formulations (Baynes et al (2005) 44(12):4919-25; EP1478394). Being a polar additive, it prevents the aggregation of protein folding intermediates.

Like L-arginine, L-lysine is capable of significantly preventing heat- and dilution-induced aggregration of lysozyme (Shiraki et al (2002) J Biochem, 132(4):591-5). L-proline has been established as a stabilizer in liquid immunoglobulin preparations like Sandoglobulin® or Privigen®. As an hydrophobic amino acid, it is assumed to interfere with hydrophobic protein-protein interactions and thus protects IgG from denaturation and aggregation. Besides, L-proline exhibits a good safety record when administered to patients with primary immunodeficiencies and was found to represent an amino acid of low toxicity in animal studies (Bolli et al, (2001) Biologicals, 38(1):150-7).

Recent studies contemplate citrate buffer as beneficial in monoclonal antibody formulations as it efficiently minimizes degradations like asparagine deamidations (Zheng and Janis, (2006) Int J Pharm, 308(1-2):46-51). Another advantage of citrate buffer is its capacity to stabilize pH during freezing while the established phosphate buffer system shows the greatest change in pH when lowering temperatures from +25 to −30 degrees C. (Kolhe et al, (2010) Biotechnol Prog, 26(3):727-33).

Fusion proteins may generate a variety of degraded and aggregated products which subsequently may lead to reduced activity and even adverse effects like immunogenicity. Thus, there is still a need for a stable liquid formulation of the fusion protein TNFR:Fc.

Such a formulation shall fulfil a variety of tasks. It has to be physiologically acceptable and preferably provides an environment which guarantees stability of the biopharmaceutical drug in a therapeutically effective concentration. Furthermore, the formulation shall enable a satisfactory shelf-life of the drug.

It is thus the object of the present invention to provide pharmaceutical formulations for TNFR:Fc which can be used as an alternative to those formulations known from prior art. Another object of the present invention is to provide pharmaceutical formulations for TNFR:Fc which are advantageous compared to formulations known from prior art. It is yet another object of the present invention to provide pharmaceutical formulations for TNFR:Fc which cause less drug aggregation than formulations known from prior art.

The present invention demonstrates that, by replacing, e.g., the commonly used phosphate buffer to a citrate buffer system and the stabilizer arginine to lysine, the physical stability of TNFR:Fc can be significantly improved. The proposed buffer citric acid and stabilizer lysine protect TNFR:Fc against degradation induced by mechanical and temperature stress (25 and 40° C.) and at intended storage at 2-8° C. protein degradation was significantly lower in proposed formulations compared to the commonly used phosphate buffered formulations. Therefore, the quality parameters relating to physical stability of the product could be improved. The increased physical stability of the drug product enables a prolonged shelf-life compared to the common product formulations and ensures product safety.

SUMMARY OF THE INVENTION

In a first aspect, the invention relates to a pharmaceutical composition, comprising TNFR:Fc, a citrate buffer and an amino acid selected from the group consisting of lysine and proline and their pharmaceutical acceptable salts.

In a second aspect, the invention pertains to a kit comprising a composition according to the first aspect and instructions for use of said composition.

In still a third aspect, the invention relates to a method of producing a pharmaceutical composition according to the first aspect, comprising combining TNFR:Fc, a citrate buffer and an amino acid selected from the group consisting of lysine and proline and their pharmaceutical acceptable salts.

In a final aspect, the invention also relates to a composition according to the first aspect for use in a medical treatment, in particular in a treatment of a disease selected from an autoimmune disease, ankylosing spondylitis, juvenile rheumatoid arthritis, psoriasis, psoriatic arthritis, rheumatoid arthritis, Wegener's disease (granulomatosis), Crohn's disease (or inflammatory bowel disease), chronic obstructive pulmonary disease (COPD), Hepatitis C, endometriosis, asthma, cachexia, atopic dermatitis, Alzheimer and cancer.

DETAILED DESCRIPTION OF THE PREFERRED EMBODIMENTS

The formation of degradation products during storage of TNFR:Fc seems to be the most critical attribute of the molecule. TNFR:Fc in citrate formulations displays in general a lower degradation potential, which could be due to the greater net charge of sodium citrate compared to sodium phosphate and therefore possible interaction with the charged TNFR:Fc molecule.

Accordingly, in a first aspect, the invention relates to a pharmaceutical composition, comprising TNFR:Fc, a citrate buffer and an amino acid selected from the group consisting of lysine and proline and their pharmaceutical acceptable salts.

Tumor Necrosis Factor alpha (TNF-alpha) is a member of a group of cytokines that stimulate the acute phase reaction, and thus is a cytokine involved in systemic inflammation. TNF-alpha is able to induce inflammation, induce apoptotic cell death, and to inhibit tumorgenesis and viral replication. Dysregulation of TNF-alpha production has been implicated in a variety of human diseases like autoimmune disease, ankylosing spondylitis, juvenile rheumatoid arthritis, psoriasis, psoriatic arthritis, rheumatoid arthritis, Wegener's disease (granulomatosis), Crohn's disease or inflammatory bowel disease, chronic obstructive pulmonary disease (COPD), Hepatitis C, endometriosis, asthma, cachexia, atopic dermatitis, Alzheimer as well as cancer.

Its receptor molecules include, TNFR1 (TNF receptor type 1; CD120a; p55/60; for human: RefSeq (mRNA): NM_001065, RefSeq (protein): NP_001056 (SEQ ID NO:1)) and TNFR2 (TNF receptor type 2; CD120b; p75/80; for human: RefSeq (mRNA): NM_001066, RefSeq (protein): NP_001057 (SEQ ID NO:2)). TNF-R1 is expressed in most tissues and can be fully activated by both the membrane-bound and soluble trimeric forms of TNF, whereas TNF-R2 is found only in cells of the immune system and responds to the membrane-bound form of the TNF homotrimer. Upon contact with TNF-alpha, TNF receptors form trimers and thereby initiate intracellular cell signaling.

Accordingly, soluble TNFR molecules or fragments thereof, which are able to bind to TNF-alpha, can be used as a competitive inhibitor for TNF-alpha. The present invention relates to such soluble TNFR molecules fused to an Fc portion of a human immunoglobulin (TNFR:Fc).

In the context of the present invention, the TNFR part of TNFR:Fc refers to any TNFR polypeptide having at least 90%, preferably at least 91%, such as at least 92% or at least 93%, more preferably at least 94%, such as at least 95%, or at least 96%, even more preferably at least 97%, such as at least 98%, or at least 99%, and most preferably 100% identity to an amino acid sequence comprising at least 150-250, preferably at least 175-245 of TNFR1 or TNFR2, preferably TNFR2, more preferably 200-240, and most preferably 225-235 amino acids of the extracellular part of TNFR2, and still binding to TNF-alpha, as determined by ELISA or any other convenient assay. More preferably, the said TNFR is capable of binding to TNF-alpha and Lymphotoxin alpha (LT-alpha), as determined by ELISA or any other convenient assay. Such assays are well-known to the skilled person.

Generally, a polypeptide has "at least x % identity" over a defined length of amino acids with another polypeptide if the sequence in question is aligned with the best matching sequence of the amino acid sequence and the sequence identity between those to aligned sequences is at least x %. Such an alignment can be performed using for example publicly available computer homology programs such as the "BLAST" program, such as "blastp" provided at the NCBI homepage at http://www.ncbi.nlm.nih.gov/blast/blast.cgi, using the default settings provided therein. Further methods of calculating sequence identity percentages of sets of polypeptides are known in the art.

The Fc-region (fragment crystallisable region) refers to the tail region of an antibody, in the case of IgG composed of the second and third constant domain of the antibody's two heavy chains. In certain embodiments, the Fc polypeptide comprises the constant region of an IgG class heavy chain or a fragment and/or variant thereof and in other embodiments the constant region of other immunoglobulin isotypes can be used to generate such TNFR:Fc fusions. For example, a TNFR:Fc polypeptide comprising the constant region of an IgM class heavy chain or a fragment and/or variant thereof could be used. Preferably, the Fc fragment is derived from IgG, more preferably from IgG1, even more preferably from human IgG1. The constant region of immunoglobulin heavy chains, with a specific example of a human IgG1 class heavy chain constant domain provided by SEQ ID NO: 3, comprises a CH1 domain (amino acids 1 through 98 of SEQ ID NO:3), a hinge region (amino acids 99 through 110 of SEQ ID NO:3), a CH2 domain (amino acids 111 through 223 of SEQ ID NO:3), and a CH3 domain (amino acids 224 through 330 of SEQ ID NO:3). As used herein, an Fc domain can contain one or all of the heavy chain CH1, hinge, CH2, and CH3 domains described above, or fragments or variants thereof. Certain embodiments of the invention include TNFR:Fc comprising all or a portion of the extracellular domain of TNFR1 (SEQ ID NO: 1) or TNFR2 (SEQ ID NO:2) fused to all or a portion of SEQ ID NO:3, optionally with a linker polypeptide between the TNFR portion and the Fc portion of the TNFR:Fc. For example, CH1, CH2 and the entire hinge region may be present in the molecule. In further embodiments, a heavy chain constant region comprising at least a portion of CH1 is the Fc portion of a TNFR:Fc. Certain embodiments can also include, for example, all of the hinge region or the C-terminal half of the hinge region to provide a disulfide bridge between heavy chains. For example, CH1 may be present along with the first seven amino acids of the hinge (amino acids 99 through 105 of SEQ ID NO: 3). In certain embodiments of this invention, the TNFR polypeptide is covalently linked, optionally through a polypeptide linker, to the N-terminus of at least one portion of a CH1 region of a heavy chain constant domain to form a TNFR:Fc.

If a dimeric TNFR:Fc is desired, it is important to include the portion of the hinge region implicated in disulfide bond formation between the heavy chains (for example, a portion of amino acids 99 through 110 of SEQ ID NO: 3 that includes amino acid 109 of SEQ ID NO: 3). In further embodiments of the invention, the TNFR:Fc can comprise portions of the CH3 domain that do not include the C-terminal lysine residue (amino acid 330 of SEQ ID NO: 3), as this residue has been observed to be removed in post-translational processing of IgG heavy chain polypeptides. Fc fusions and Fc fragments are well-known in the art.

Preferably, the TNFR:Fc is essentially identical/similar to Etanercept, more preferably, the TNFR:Fc is Etanercept.

Etanercept is a dimer of two molecules of the extracellular portion of the p75 TNF-alpha receptor, each molecule consisting of a 235 amino acid TNFR-derived polypeptide that is fused to a 232 amino acid Fc portion of human IgG1. The amino acid sequence of the monomeric component of etanercept is shown as SEQ ID NO:4. In the dimeric form of this molecule, two of these fusion polypeptides (or "monomers")

are held together by three disulfide bonds that form between the immunoglobulin portions of the two monomers. The etanercept dimer therefore consists of 934 amino acids, and has an apparent molecular weight of approximately 150 kilodaltons. In North America, etanercept is co-marketed by Amgen and Pfizer under the trade name Enbrel® in two separate formulations, one in powder form, the other as a pre-mixed liquid. Wyeth is the sole marketer of Enbrel® outside of North America excluding Japan where Takeda Pharmaceuticals markets the drug.

The term "essentially identical/similar to Etanercept" as used herein means that the amino acid sequence of the TNFR:Fc has at least 95% identity to the amino acid sequence shown in SEQ ID NO: 4, more preferably at least 96% identity, such as 97% identity, and most preferably 98% identity, such as 99% identity to the amino acid sequence shown in SEQ ID NO: 4. Alternatively or additionally, the TNFR:Fc may (only) differ from Etanercept by posttranslational modifications, e.g. by glycosylation. Suitable procedures for changing a glycosylation pattern, such as introducing or deleting a glycosylation site, and tests for determining a glycosylation pattern are well known to the skilled person.

The TNFR:Fc may be recombinantly produced, preferably by using a mammalian cell based expression system. Preferably, said mammalian cell-based expression system is at least one selected from the group consisting of Baby hamster Kidney cell lines (e.g., BHK21); Chinese hamster ovary cell lines (e.g., CHO-K1, CHO-DG44, CHO-DXB, or CHO-dhfr-); Murine myeloma cell lines (e.g., SP2/0); Mouse myeloma cell lines (e.g., NS0); Human embryonic kidney cell lines (e.g., HEK-293); Human-retina-derived cell lines (e.g., PER-C6), and/or Amniocyte cell lines (e.g., CAP). Preferably, hamster cell based expression systems are being used. BHK21 ("Baby Hamster Kidney") cells belong to a quasi diploid established line of Syrian hamster cells, descended from a clone from an unusually rapidly growing primary culture of newborn hamster kidney tissue. Non limiting examples for BHK-21 cell lines which are commercially available and can be used in the context of the present invention are BHK-21 (C-13); BHK21-pcDNA3.1-HC; BHK570; Flp-In-BHK Cell Line; and/or BHK 21 (Clone 13) hamster cell line.

Chinese hamster ovary (CHO) cells are a cell line derived from the ovary of the Chinese hamster. They are often used in biological and medical research and are commercially utilized in the production of therapeutic proteins. They were introduced in the 1960s and were originally grown as a monolayer culture. Today, CHO cells are the most commonly used mammalian hosts for industrial production of recombinant protein therapeutics and are usually grown in suspension culture.

Non limiting examples for CHO cell lines which are commercially available and can be used in the context of the present invention are FreeStyle CHO-S cells; ER-CHO Cell Line; CHO 1-15 500 CHINESE HAM; CHO-DXB, CHO-dhfr-, CHO DP-12 clone#1934; CHO-CD36; CHO-ICAM-1; CHO-K1; Ovary; HuZP3-CHOLec3.2.8.1; xrs5; CHO-K1/BB2 Cells; CHO-K1/BB3 Cells; CHO-K1/EDG8/Galpha15 Cells; CHO-K1/M5 Cells; CHO-K1/NK1 Cells; CHO-K1/NK3 Cells; CHO-K1/NMUR1 Cells; CHO-K1/NTSR1 Cells; CHO-K1/OX1 Cells; CHO-K1/PAC1/Ga15 Cells; CHO-K1/PTAFR Cells; CHO-K1/TRH1 Cells; CHO-K1N1B Cells; 5HT1A Galpha-15-NFAT-BLA CHO-K1 Cell Line; AVPR2 CRE-BLA CHO-K1 Cell Line; CHO-S Cells SFM Adapted; DG44 Cells; Flp-In-CHO Cell Line; Gene-Switch-CHO Cell Line; NFAT-bla CHO-K1 Cell Line; T-REx-CHO Cell Line; GenoStat CHO K-1 Stable Cell Line; GenoStat CHO K-1 Stable Cell Line Kit; CHO-K1 Cell Line hamster, CHO-PEPT1 Cell line, CHO SSF3 and/or CHO-HPT1 Cell Line. In a particularly preferred embodiment, the hamster cell-based expression system is a CHO-dhfr-cell line.

The pharmaceutical composition may comprise TNFR:Fc at a concentration from 0.1 mM to 0.7 mM, such as 0.2 mM or 0.6 mM, preferably at a concentration from 0.15 mM to 0.5 mM, such as 0.4 mM or 0.45 mM, more preferably at a concentration from 0.25 mM to 0.35 mM, such as about 0.3 mM.

The citrate buffer may be any suitable citrate buffer. For example, the citrate buffer may comprise or consist of sodium citrate, potassium citrate, citric acid, or mixtures thereof. The citrate buffer seems to have the greatest influence on the stability of the formulation. The increased stability of a 50 mM citrate buffer formulation compared to 25 mM citrate buffer formulation is shown in the examples. An increase up to at least 120 mM could lead to even increased effects. A minimum of 25 mM citrate buffer seems to be mandatory for the stabilization. Accordingly, the pharmaceutical composition may comprise the citrate buffer at a concentration from 25 mM to 120 mM, such as from 30 mM to 115 mM, preferably at a concentration from 40 mM to 110 mM, such as from 45 mM to 105 mM, more preferably at a concentration from 50 mM to 100 mM, such as at a concentration of 55 mM, 60 mM, 65 mM, 70 mM, 75 mM, 80 mM, 85 mM, 90 mM, or 95 mM. In another preferred embodiment, the pharmaceutical composition comprises the citrate buffer at a concentration as indicated in the compositions described in the Examples section.

The pH is preferably a value of 5 to 7.5, such as from 5.5 to 7, even more preferably from 6 to 6.6, such as 6.1 to 6.5, most preferably from 6.2 to 6.4, such as about 6.3. It is noted that although the pH is preferably a value of 5 to 7.5, alternatively lower pH values of up to 2.8, e.g. in the range of 2.8 to 4.0 may alternatively also be employed. The pharmaceutical composition comprises an amino acid selected from the group consisting of lysine and proline and their pharmaceutical acceptable salts, such as hydrochlorides. The amino acid may be in D-, L- or DL-configuration, preferably in L-configuration.

At the addition of about 25 mM the additional effect of the combination with the basic amino acid lysine is striking. The addition of up to 100 mM lysine is believed to have an additional effect. Thus, the pharmaceutical composition may comprise the amino acid at a concentration from 15 mM to 100 mM, preferably at a concentration from 20 mM to 90 mM, more preferably at a concentration from 25 mM to 75 mM. In another preferred embodiment, the pharmaceutical composition comprises the amino acid at a concentration as indicated in the compositions described in the Examples section. In a particularly preferred embodiment, the amino acid is lysine, or its pharmaceutical acceptable salts.

In addition, the pharmaceutical composition may further comprise at least one tonicity modifier. As used herein, the term "tonicity modifier" is intended to describe a molecule other than citrate, lysine or proline that contributes to the osmolality of a solution. Preferably, the osmolality of a pharmaceutical composition is regulated in order to stabilize the active ingredient and in order to minimize the discomfort to the patient upon administration. Generally, it is preferred that a pharmaceutical composition be isotonic with serum by having the same or similar osmolality, i.e. an osmolality from about 180 to 480 mosmol/kg. Preferably, the at least one tonicity modifier is selected from the group consisting of sodium chloride, cysteine, histidine, glycine, potassium chloride, sucrose, glucose and mannitol, more preferably the tonicity modifier is sodium chloride and/or sucrose. The pharmaceutical composition may comprise the at least one tonicity modifier at a total concentration from 5 mM to 200 mM, such as from 10 mM to 190 mM, from 15 mM to 180 mM, from 20 mM to 170 mM, from 25 mM to 160 mM, from 30 mM to 150 mM, from 35 mM to 140 mM, from 40 mM to 130 mM, or from 45 mM to 120 mM, e.g. 110 mM, but preferably at a concentration from 50 mM to 100 mM. In another preferred embodiment, the pharmaceutical composition comprises the tonicity modifier(s) at a concentration as indicated in the compositions described in the Examples section.

Further, the pharmaceutical composition may comprise at least one excipient. The term "excipient" as used herein refers to a pharmacologically inactive substance used as a carrier for the active agent in a pharmaceutical composition. In some cases, an "active" substance may not be easily administered and absorbed by the human body. In such cases the substance in question may be mixed with an excipient or dissolved in an excipient solution. Excipients are also sometimes used to bulk up formulations that contain very potent active ingredients, in order to facilitate a convenient and accurate dosing. In addition to their use in the single-dosage quantity, excipients can be used in the manufacturing process to optimize the handling of the concerned active substance. Depending on the route of administration and the form of the pharmaceutical composition, different excipients may be used. Thus, excipients may comprise inter alia antiadherents, binders, colours and preservatives such as antioxidants.

For example, at least one excipient may be selected from the group consisting of lactose, glycerol, xylitol, sorbitol, mannitol, maltose, inositol, trehalose, glucose, bovine serum albumin (BSA), dextran, polyvinyl acetate (PVA), hydroxypropyl methylcellulose (HPMC), polyethyleneimine (PEI), gelatin, polyvinylpyrrolidone (PVP), hydroxyethylcellulose (HEC), polyethylene glycol (PEG), ethylene glycol, glycerol, dimethysulfoxide (DMSO), dimethylformamide (DMF), L-serine, sodium glutamate, alanine, glycine, sarcosine, gamma-aminobutyric acid (GABA), polyoxyethylene sorbitan monolaurate (Tween-20), polyoxyethylene sorbitan monooleate (Tween-80), sodium dodecyl sulphate (SDS), polysorbate, polyoxyethylene copolymer, potassium phosphate, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate and 2-O-beta-mannoglycerate. In one preferred embodiment, the excipient may be chosen from those described in the Examples section.

The pharmaceutical composition may comprise the at least one excipient at a total concentration of at least 0.1 mM, e.g. from 0.1 mM to 07 mM, such as at a concentration of 0.6 mM, preferably at a concentration from 0.15 mM to 0.5 mM, such as from 0.2 mM to 0.4 mM, more preferably at a concentration from 0.24 mM to 0.34 mM. In another preferred embodiment, the pharmaceutical composition comprises the excipient at a concentration as indicated in the compositions described in the Examples section.

Preferably, the composition is liquid. However, in another embodiment, the pharmaceutical composition may be lyophilized, and can be reconstituted, for example by the addition of water, forming a liquid composition. Hence, the pharmaceutical composition may further comprise a pharmaceutically acceptable solvent. In a preferred embodiment, the pharmaceutically acceptable solvent is water. The concentrations of components presented herein refer to a liquid formulation as well as to a constituted lyophilate or a formulation to be lyophilised.

Excipients might display a protective effect during freezing of lyophilized formulations, so called cryoprotective features. Furthermore, metal chelating agents and tensides can be added. Some agents may have a double role, e.g., some sugars or sugar alcohols can serve for example as excipient, cryoprotective and/or tonifying agent.

The present formulation in aqueous state is ready to use, while the lyophilized state of the present formulation can be transferred into liquid formulations by e.g. addition of water for injection.

Particularly preferred compositions comprise or consist of 0.1 mM to 0.7 mM TNFR:Fc, e.g. Etanercept, 25 mM to 120 mM citrate buffer, e.g. sodium citrate, 15 mM to 100 mM lysine, e.g. lysine hydrochloride, 10 mM to 100 mM sucrose and 5 mM to 200 mM sodium chloride at a pH value of about 6.3.

Alternatively, the pharmaceutical composition may comprise or consist of 0.3 mM TNFR:Fc, e.g. Etanercept, 50 mM citrate buffer, e.g. sodium citrate, 25 mM lysine, e.g. lysine hydrochloride, 29 mM sucrose and 75 mM sodium chloride at a pH value of about 6.3.

In still another preferred embodiment, the pharmaceutical composition may comprise or consist of 0.3 mM TNFR:Fc, e.g. Etanercept, 25 mM citrate buffer, e.g. sodium citrate, 25 mM lysine, e.g. lysine hydrochloride, 29 mM sucrose and 88 mM sodium chloride at a pH value of about 6.3.

However, the pharmaceutical composition may also comprise or consist of 0.1 mM to 0.7 mM TNFR:Fc, e.g. Etanercept, 25 mM to 120 mM citrate buffer, e.g. sodium citrate, 15 mM to 100 mM proline, 10 mM to 100 mM sucrose and 5 mM to 200 mM sodium chloride at a pH value of about 6.3.

Finally, the pharmaceutical composition may also comprise or consist of 0.3 mM TNFR:Fc, e.g. Etanercept, 25 mM citrate buffer, e.g. sodium citrate, 25 mM proline, 29 mM sucrose and 75 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 120 mM citrate buffer, e.g. sodium citrate, 25 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 120 mM citrate buffer, e.g. sodium citrate, 50 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride, 29 mM sucrose and 51 mM sodium chloride at a pH value of about 6.3.

The pharmaceutical composition may also comprise or consist of 0.3 mM TNFR:Fc, e.g. Etanercept, 120 mM citrate buffer, e.g. sodium citrate, 25 mM lysine, e.g. lysine hydrochloride, 29 mM sucrose and 22 mM sodium chloride at a pH value of about 6.3.

The pharmaceutical composition may also comprise or consist of 0.3 mM TNFR:Fc, e.g. Etanercept, 120 mM citrate buffer, e.g. sodium citrate, 50 mM lysine, e.g. lysine hydrochloride and 29 mM sucrose at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride and 75 mM sodium chloride at a pH value of about 6.3.

The pharmaceutical composition may also comprise or consist of 0.3 mM TNFR:Fc, e.g. Etanercept, 120 mM citrate buffer, e.g. sodium citrate, 25 mM lysine, e.g. lysine hydrochloride and 36 mM sodium chloride at a pH value of about 6.3.

The pharmaceutical composition may also comprise or consist of 0.3 mM TNFR:Fc, e.g. Etanercept, 120 mM citrate buffer, e.g. sodium citrate, 50 mM lysine, e.g. lysine hydrochloride and 17 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 25 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 50 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 25 mM lysine, e.g. lysine hydrochloride, 29 mM sucrose and 56 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 50 mM lysine, e.g. lysine hydrochloride, 29 mM sucrose and 31 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 25 mM lysine, e.g. lysine hydrochloride, 19 mM sucrose and 75 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 50 mM lysine, e.g. lysine hydrochloride and 59 mM sodium chloride at a pH value of about 6.3.

The pharmaceutical composition may also comprise or consist of 0.3 mM TNFR:Fc, e.g. Etanercept, 25 mM citrate buffer, e.g. sodium citrate, 25 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 25 mM citrate buffer, e.g. sodium citrate, 50 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 25 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride, 29 mM sucrose and 48 mM sodium chloride at a pH value of about 6.3.

The pharmaceutical composition may also comprise or consist of 0.3 mM TNFR:Fc, e.g. Etanercept, 25 mM citrate buffer, e.g. sodium citrate, 25 mM lysine, e.g. lysine hydrochloride, 29 mM sucrose and 88 mM sodium chloride at a pH value of about 6.3.

The pharmaceutical composition may also comprise or consist of 0.3 mM TNFR:Fc, e.g. Etanercept, 25 mM citrate buffer, e.g. sodium citrate, 25 mM proline, 29 mM sucrose and 88 mM sodium chloride at a pH value of about 6.3.

The pharmaceutical composition may also comprise or consist of 0.3 mM TNFR:Fc, e.g. Etanercept, 25 mM citrate buffer, e.g. sodium citrate, 25 mM proline, 29 mM sucrose and 100 mM sodium chloride at a pH value of about 6.3.

The pharmaceutical composition may also comprise or consist of 0.3 mM TNFR:Fc, e.g. Etanercept, 25 mM phosphate buffer, e.g. sodium citrate, 25 mM lysine, e.g. lysine hydrochloride, 29 mM sucrose and 88 mM sodium chloride at a pH value of about 6.3.

The pharmaceutical composition may also comprise or consist of 0.3 mM TNFR:Fc, e.g. Etanercept, 25 mM phosphate buffer, e.g. sodium citrate, 25 mM lysine, e.g. lysine hydrochloride, 29 mM sucrose and 75 mM sodium chloride at a pH value of about 6.3.

The pharmaceutical composition may also comprise or consist of 0.3 mM TNFR:Fc, e.g. Etanercept, 50 mM citrate buffer, e.g. sodium citrate, 50 mM lysine, e.g. lysine hydrochloride, 29 mM sucrose and 50 mM sodium chloride at a pH value of about 6.3.

The pharmaceutical composition may also comprise or consist of 0.3 mM TNFR:Fc, e.g. Etanercept, 75 mM citrate buffer, e.g. sodium citrate, 25 mM lysine, e.g. lysine hydrochloride, 29 mM sucrose and 50 mM sodium chloride at a pH value of about 6.3.

The pharmaceutical composition may also comprise or consist of 0.3 mM TNFR:Fc, e.g. Etanercept, 65 mM citrate buffer, e.g. sodium citrate, 25 mM lysine, e.g. lysine hydrochloride, 29 mM sucrose and 55 mM sodium chloride at a pH value of about 6.3.

Preferably, the pharmaceutical composition is a stable liquid composition. The term "stable" as used herein means that the TNFR:Fc exhibits one or more of the following features:

(i) exhibiting less than 99% aggregation products (SUM APs) as compared to the same TNFR:Fc formulated in the commonly used phosphate buffered formulation containing 0.3 mM Etanercept in a matrix consisting of 25 mM phosphate buffer, 25 mM arginine and sodium chloride in a molarity greater than 75 mM or in a the amount needed to adjust isotonicity, more preferably less than 98.5% SUM APs, even more preferably less than 98% SUM APs, most preferably less than 97.5% SUM APs, as determined after three months of storage at 40° C. by SEC;

(ii) and/or exhibiting less than 99% degradation products (SUM DPs) as compared to the same TNFR:Fc formulated in the commonly used phosphate buffered formulation containing 0.3 mM etanercept in a matrix consisting of 25 mM phosphate buffer, 25 mM Arginine and sodium chloride in a molarity greater than 75 mM or in a the amount needed to adjust isotonicity, more preferably less than 98% SUM DPs, such as less than 97% SUM DPs, even more preferably less than 96% SUM DPs, such as less than 95% SUM DPs, most preferably less than 94% SUM DPs, such as less than 93% SUM DPs, as determined after three months of storage at 40° C. by SEC.

Thus, the pharmaceutical formulation according to the invention may be suitably formulated for long term storage. As used herein, the term "long term storage" shall refer to storage of a composition comprising the pharmaceutical formulation for more than 1 month, preferably for more than 2, 3, 4, 5, 6, 7, 8, 9, 10, 11 or even 12 months.

As exemplified below, stability of formulations containing either a citrate or phosphate buffer system in combination with either lysine or proline as stabilizer were assessed during a three month-stability study at intended (2-8° C.) as well as accelerated storage condition (25 and 40° C.). Formulations containing the citrate buffer system were thereby determined to be superior compared to formulations containing the phosphate buffer system regarding the formation of post peaks (as determined e.g. by RPC), the formation of degradation products (as determined e.g. by SEC) and the formation of acid peaks (as determined e.g. by CEX).

The described effects were partially even more pronounced, including the superior stabilization of TNFR:Fc formulated in the citrate/lysine formulation matrix, if formulations were stored in vials, displaying a greater liquid/air interaction surface. Determination of the stability of a liquid composition is further exemplified in the examples section, and in particular in Example 3.

The pharmaceutical composition according to the first aspect can be used in a medical treatment. Diseases which may be treated by using the pharmaceutical composition of the invention include, but are not limited to autoimmune diseases, ankylosing spondylitis, juvenile rheumatoid arthritis, psoriasis, psoriatic arthritis, rheumatoid arthritis, Wegener's disease (granulomatosis), Crohn's disease or inflammatory bowel disease, chronic obstructive pulmonary disease (COPD), Hepatitis C, endometriosis, asthma, cachexia, atopic dermatitis, Alzheimers disease and cancer. Accordingly, also contemplated is a method of treatment, comprising administering the composition according to the first aspect to a subject in need thereof, e.g. a subject suffering from one of the above mentioned diseases.

Dosage of the TNFR:Fc will depend on the disease, severity of condition, patient's clinical history, and response to the (prior) therapy, and will be adjusted and monitored by a physician. The pharmaceutical composition may be administered parenterally, such as subcutaneously, intramuscularly, intravenously, intraperitoneally, intracerebrospinally, intra-articularly, intrasynovially and/or intrathecally by either bolus injection or continuous infusion.

The dosage of TNFR:Fc per adult may range from about 1-500 mg/m$^2$, or from about 1-200 mg/m$^2$, or from about 1-40 mg/m$^2$ or about 5-25 mg/m$^2$. Alternatively, a flat dose may be administered, wherein the amount may range from 2-500 mg/dose, 2-100 mg/dose or from about 10-80 mg/dose. The dose may be administered more than one time per week, such as two or more times per week at a dose range of 25-100 mg/dose. In another embodiment, an acceptable dose for administration by injection contains 80-100 mg/dose, e.g. 80 mg per dose. The doses can be administered weekly, biweekly or separated by several weeks, e.g. by three weeks.

It is further contemplated that an improvement of the patient's condition will be obtained by a dose of up to 100 mg of the pharmaceutical composition one to three times per week over a period of at least three weeks, though treatment for longer periods may be necessary to induce the desired degree of improvement. However, for incurable chronic conditions the regimen may be continued indefinitely. A suitable regimen for paediatric patients (ages 4-17) may involve a dose of 0.4 mg/kg to 5 mg/kg of TNFR:Fc, administered one or more times per week.

More specifically, in the case of rheumatoid arthritis, 25 mg TNFR:Fc may be administered twice weekly. Alternatively, 50 mg administered once weekly has been shown to be safe and effective.

In the case of psoriatic arthritis and ankylosing spondylitis, the recommended dose is 25 mg TNFR:Fc administered twice weekly or 50 mg administered once weekly.

Turning to plaque psoriasis, the recommended dose of TNFR:Fc is 25 mg administered twice weekly or 50 mg administered once weekly. Alternatively, 50 mg given twice weekly may be used for up to 12 weeks followed, if necessary, by a dose of 25 mg twice weekly or 50 mg once weekly. Treatment with TNFR:Fc should continue until remission is achieved, for up to 24 weeks. Continuous therapy beyond 24 weeks may be appropriate for some adult patients. Treatment should be discontinued in patients who show no response after 12 weeks. If re-treatment with TNFR:Fc is indicated, the same guidance on treatment duration should be followed. The dose should be 25 mg twice weekly or 50 mg once weekly.

Regarding juvenile idiopathic arthritis (age 4 years and above), 0.4 mg/kg (up to a maximum of 25 mg per dose) after reconstitution of 25 mg TNFR:Fc in 1 ml of solvent, may be given twice weekly as a subcutaneous injection with an interval of 3-4 days between doses.

Concerning paediatric plaque psoriasis (age 8 years and above), 0.8 mg/kg (up to a maximum of 50 mg per dose) once weekly for up to 24 weeks may be administered. Treatment should be discontinued in patients who show no response after 12 weeks. If re-treatment with TNFR:Fc is indicated, the above guidance on treatment duration should be followed. The dose should be 0.8 mg/kg (up to a maximum of 50 mg per dose) once weekly.

In case of renal and hepatic impairment no dose adjustment is required.

In a second aspect, the invention relates to a kit comprising a composition according to the first aspect and instructions for use of the present composition.

In a preferred embodiment, the composition is contained in a pre-filled syringe. In another preferred embodiment, the composition is contained in a pre-filled vial. The kit may comprise one or more unit dosage forms containing the pharmaceutical composition of the invention. Examples for suitable syringes are BD Hypak SCF 1 ml long, glass pre-fillable syringes assembled with PTFE coated stoppers (rubber quality 4023/50 from West). The glass vials may be for example 6R glass vials (hydrolytic class I) assembled with PTFE coated stoppers (rubber quality 4023/50 from West). However, any other suitable syringe or vial may be used. The kit may also comprise the pharmaceutical composition according to the invention in another secondary container, such as in an autoinjector.

The prefilled syringe may contain the formulation in aqueous form. Described syringe may be further supplied with an autoinjector, which often is a disposable article for single use only, and may e.g. have a volume between 0.1 and 1 ml. However, the syringe or autoinjector may also be for multi-usage or multi-dosing. The described vial may contain the formulation in lyophilised or aqueous state, and may serve as a single or multiple use device. The vial may e.g. have a volume between 1 and 10 ml.

In a third aspect, the invention pertains to a method of producing a pharmaceutical composition according to the first aspect, comprising combining TNFR:Fc, a citrate buffer and an amino acid selected from the group consisting of lysine and proline and their pharmaceutical acceptable salts.

In one particular embodiment, the method may comprise a further step of adding a pharmaceutically acceptable solvent as defined above. The method may further comprise the step of adding at least one tonicity modifier, such as sodium chloride and/or sucrose, and optionally an excipient as defined above. In a final preferred embodiment, the method may further comprise a lyophilization step, which step may be before or after adding the at least one tonicity modifier, and/or an excipient as defined above.

The invention will be more fully understood by reference to the following examples. However, the examples should not be construed as limiting the scope of the invention.

EXAMPLES

Description of Materials

The TNFR:Fc which was used for the described examples, is derived from recombinant CHO cells, which have been cultured in a fed-batch process in chemically defined medium. The TNFR:Fc is purified from the cell free harvest by standard methods including affinity chromatography on protein A resins and by further chromatographic and filtration steps.

The invention claimed is:

1. A pharmaceutical composition, comprising TNFR:Fc, a citrate buffer and an amino acid or a pharmaceutically acceptable salt thereof, the amino acid being lysine or proline; wherein the citrate buffer is at a concentration from 25 mM to 120 mM and the amino acid is at a concentration from 15 mM to 100 mM.

2. The pharmaceutical composition of claim 1, wherein the amino acid is lysine or a pharmaceutically acceptable salt thereof.

3. The pharmaceutical composition of claim 1, further comprising a tonicity modifier, wherein the tonicity modifier is selected from the group consisting of sodium chloride, cysteine, histidine, glycine, potassium chloride, sucrose, glucose and mannitol.

4. The pharmaceutical composition of claim 3, comprising at least one tonicity modifier at a total concentration from 5 mM to 200 mM.

5. The pharmaceutical composition of claim 1, further comprising at least one excipient, wherein the at least one excipient is selected from the group consisting of lactose, glycerol, xylitol, sorbitol, mannitol, maltose, inositol, trehalose, glucose, bovine serum albumin (BSA), dextran, polyvinyl acetate (PVA), hydroxypropyl methylcellulose (HPMC), polyethyleneimine (PEI), gelatine, polyvinylpyrrolidone (PVP), hydroxyethylcellulose (HEC), polyethylene glycol (PEG), ethylene glycol, glycerol, dimethysulfoxide (DMSO), dimethylformamide (DMF), L-serine, sodium glutamate, alanine, glycine, sarcosine, gamma-aminobutyric acid (GABA); polyoxyethylene sorbitan monolaurate, preferably Tween-20; polyoxyethylene sorbitan monooleate, preferably Tween-80; sodium dodecyl sulphate (SDS), polysorbate, polyoxyethylene copolymer, potassium phosphate, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, and 2-O-beta-mannoglycerate.

6. The pharmaceutical composition of claim 5, comprising the at least one excipient at a total concentration from 0.1 mM to 0.7 mM.

7. The pharmaceutical composition of claim 1, comprising TNFR:Fc at a concentration from 0.1 mM to 0.7 mM.

8. The pharmaceutical composition of claim 1, wherein said composition further comprises a pharmaceutically acceptable solvent.

9. The pharmaceutical composition of claim 1, wherein the composition is lyophilized.

10. The pharmaceutical composition of claim 1,
consisting essentially of 0.1 mM to 0.7 mM TNFR:Fc, 25 mM to 120 mM citrate buffer, 15 mM to 100 mM lysine, 10 to 100 mM sucrose and 5 mM to 200 mM sodium chloride at a pH value of about 6.3; or consisting essentially of 0.3 mM TNFR:Fc, 50 mM citrate buffer, 25 mM lysine, 29 mM sucrose and 75 mM sodium chloride at a pH value of about 6.3; or consisting essentially of 0.3 mM TNFR:Fc, 25 mM citrate buffer, 25 mM lysine, 29 mM sucrose and 88 mM sodium chloride at a pH value of about 6.3; or consisting essentially of 0.1 mM to 0.7 mM TNFR:Fc, 25 mM to 120 mM citrate buffer, 15 mM to 100 mM proline, 10 mM to 100 mM sucrose and 5 mM to 200 mM sodium chloride at a pH value of about 6.3; or consisting essentially of 0.3 mM TNFR:Fc, 25 mM citrate buffer, 25 mM proline, 29 mM sucrose and 75 mM sodium chloride at a pH value of about 6.3.

11. The pharmaceutical composition of claim 1, wherein TNFR:Fc is etanercept.

12. A kit comprising a composition of claim 1 and instructions for use of said composition, wherein the composition is contained in a pre-filled syringe or wherein the composition is contained in a pre-filled vial.

13. The pharmaceutical composition of claim 3, wherein the tonicity modifier is sodium chloride, sucrose, or a combination thereof.

14. The pharmaceutical composition of claim 1, wherein the pharmaceutical composition is free of a phosphate buffer and arginine.

15. The pharmaceutical composition of claim 1, wherein the pharmaceutical composition comprises:
   (i) 50 mM citrate and 25 mM lysine;
   (ii) 25 mM citrate and 25 mM lysine; or
   (iii) 25 mM citrate and 25 mM proline;
and wherein the pharmaceutical composition is free of a phosphate buffer.

16. The kit of claim 12, wherein the composition is lyophilized and contained in a vial.

* * * * *